United States Patent [19]

Johnson

[11] Patent Number: 4,753,645
[45] Date of Patent: Jun. 28, 1988

[54] PERINEAL SHIELD

[75] Inventor: Russell L. Johnson, Weyauwega, Wis.

[73] Assignee: Weyerhaeuser Company, Tacoma, Wash.

[21] Appl. No.: 97,990

[22] Filed: Sep. 17, 1987

[51] Int. Cl.⁴ .............................................. A61F 13/16
[52] U.S. Cl. ................................. 604/378; 604/385 R
[58] Field of Search .............. 604/378, 370, 366, 355, 604/385.1, 385.2

[56] References Cited

U.S. PATENT DOCUMENTS

| | | |
|---|---|---|
| 3,315,677 | 4/1967 | Tyrrell. |
| 3,890,973 | 6/1975 | Davis et al. |
| 3,995,638 | 12/1976 | Schaar. |
| 4,067,336 | 1/1978 | Johnson. |
| 4,182,334 | 1/1980 | Johnson. |
| 4,246,900 | 1/1981 | Schroder. |
| 4,505,707 | 3/1985 | Feeney ............................. 604/393 |
| 4,554,191 | 11/1985 | Korpman ........................... 428/35 |
| 4,596,244 | 6/1986 | Jackson ............................. 128/132 |
| 4,655,759 | 4/1987 | Romans-Hess et al. ............ 604/385 |

Primary Examiner—John D. Yasko

[57] ABSTRACT

A shield to be worn between the legs of a user. The shield, on its body side has a non absorbent, liquid impermeable, flexible midspan and an outside perimeter of absorbent material. In use, liquid makes contact with the shield on the flexible midspan and is moved quickly away until the liquid contacts the absorbent perimeter where it is rapidly taken up and retained. The shield is characterized by its capability to rapidly take up and contain liquids, its capability to fit comfortably and remain in place reliably, and its discreetness when carrying and wearing.

22 Claims, 3 Drawing Sheets

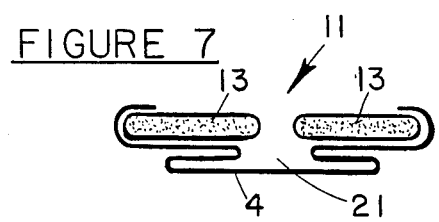
FIGURE 7
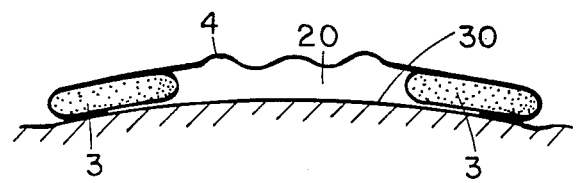
FIGURE 8
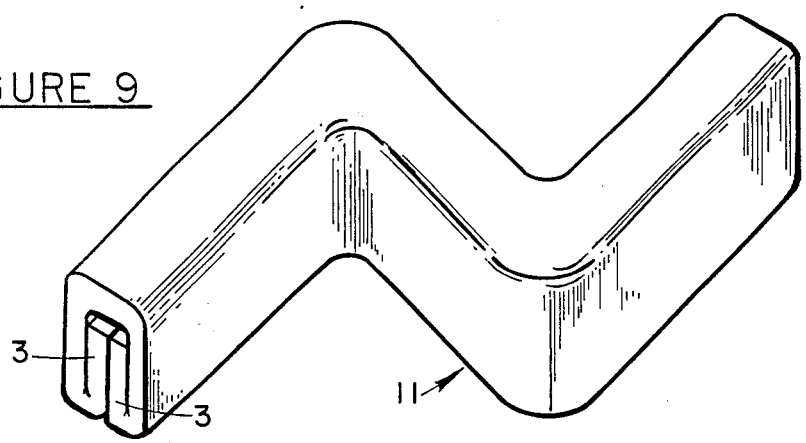
FIGURE 9
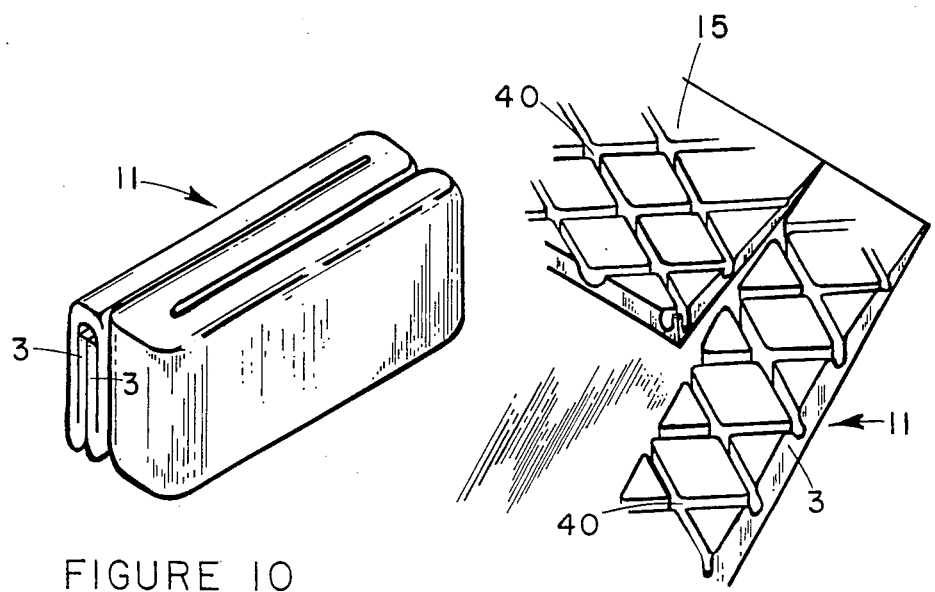
FIGURE 10
FIGURE 11

PERINEAL SHIELD

FIELD OF THE INVENTION

Shields have been worn between the legs for many reasons. Menstrual protection, diapering, incontinence of urine, and/or stools, perspiration and collection of a variety of body secretions and discharges are representative of reasons for wearing a shield between the legs.

Shields to be worn between the legs are normally use specific. However, it has long been known to employ such products for utilities other than their intended use. For example, the use of an incontinence shield for heavy flow menstrual protection.

Also, shields are often use specific within an application. For example, the market provides light duty, heavy duty, and over night menstrual protection shields.

This invention is consistent with other species of its genus in that it is use specific but has applications outside its intended use, and in that its intended use is to serve a segment of a population having the same problem but with differing needs.

Specifically, the invention is a shield to be worn between the legs to serve to intercept, collect, and retain incontinent urinary discharges of otherwise normal and fully active people with a moderate to severe urinary incontinence problem.

BACKGROUND OF THE INVENTION

Heretofore, incontinent care devices have provided an excess of absorbent material to meet the needs of incontinent users. Problems associated with bulk such as comfort, and discreetness make such products less than desirable for otherwise normal and active individuals with a moderate to severe urinary incontinence problem.

The introduction of what is commonly referred to as super absorbents into the art has permitted the provision of absorbent capacity with less bulk than conventional absorbents. However, most super absorbents have a liquid take up rate that is significantly slower than the take up rate of conventional absorbents.

A urinary discharge may reach rates of one ounce per second and a total of 8 to 12 ounces (1 to 1.5 cups) may be discharged in a time period of from 15 to 30 seconds.

To meet the requirements of secrecy and discreetness and to serve the functional needs of the user it is necessary to provide the seemingly contradictory properties of, a low dry bulk and a high liquid capacity, with a fast absorbent rate in a shield that is discreet, convenient, comfortable, and reliable in use.

OBJECTS

It is an object of this invention to provide a shield to be worn between the legs for the purpose of intercepting, distributing, collecting, and retaining a urinary discharge of moderate to severe character.

It is further an object to provide the shield described above wherein the shield is discreet, comfortable, and reliable.

It is further an object of this invention to provide the shield as described above wherein the shield is configured so as to enable the absorbent to take up liquids at rates that are greater than would be obtainable with the absorbent in the conventional, substantially uniform distribution configuration.

It is further an object of this invention to provide the shield described above wherein the shield is provided with a flexible liquid impermeable, non absorbent, receiving reservoir in the midspan of the shield to receive and distribute a urinary discharge at a rapid rate.

It is further an object of this invention to provide the shield as described above wherein the flexible midspan of the shield may serve as a high volume, short duration reservoir for liquids and will retain liquids until they can be absorbed into absorbent materials adjacent to the midspan.

Other objects will become apparent from the following specifications, drawings, and claims.

DISCUSSION OF THE PRIOR ART

This invention is novel in its mode of operation and the means employed to achieve the ends achieved. However, the prior art does provide devices which have elements in common with this invention.

The prior art, known to the inventor, which is relevant to this invention is:

| U.S. PAT. NO. | INVENTOR | DATE OF ISSUE |
|---|---|---|
| 4,067,336 | Johnson | Jan. 10, 1978 |
| 4,182,334 | Johnson | Jan. 08, 1980 |
| 3,890,973 | Davis et al | Jun. 24, 1975 |
| 4,655,759 | Romans-Hess et al | Apr. 07, 1987 |
| 3,315,677 | Tyrrell Jr. | Apr. 25, 1967 |
| 3,995,638 | Scharr | Dec. 07, 1976 |
| 4,554,191 | Koraman | Nov. 19, 1985 |
| 4,505,707 | Feeney | Mar. 19, 1985 |
| 4,596,244 | Jackson | Jun. 24, 1986 |
| 4,246,900 | Schroder | Jan. 27, 1981 |

Of these, the inventor sees as most relevant the two JOHNSON patents listed, the DAVIS patent and the ROMANS-HESS patent.

U.S. Pat. No. 4,067,336 to JOHNSON teaches a shield having four hinged panels that move in concert with the body movements of the wearer and each panel moves independently of the other three panels. These hinged panels have the effect of preventing movement of one panel from being transmitted to the other three panels.

In counterdistinction the shield of this invention employs a flexible midspan which is incapable of transmitting forces in compression and does not, in use, come under tension in its midspan and thereby prevents the transferences of forces from one quadrant of the shield to another.

U.S. Pat. No. 4,182,334 to JOHNSON teaches the provision of an absorbent reservoir which will hold liquid until the liquid can be absorbed by the absorbent of the shield. It should be noted that the reservoir of JOHNSON is functional only when the wearer's body is substantially upright and that the functionality of the reservoir is diminished or eliminated when the wearer's body is substantially horizontal.

In counterdistinction the instant invention provides a reservoir that is non absorbent and will retain liquid in all body positions until the liquid can be taken up and retained by the surrounding absorbent.

The shield of DAVIS provides a liquid impervious, non absorbent, reservoir in the expected discharge receiving area of the shield. The reservoir is overlaid with absorbent which has a slit positioned so as to permit stools to pass through the absorbent and into the reservoir. The reservoir of DAVIS is not intended to function as a liquid receiving and holding reservoir and the reservoir of DAVIS could not in the configuration taught by Davis, serve to intercept and retain a urinary discharge.

In counterdistinction the shield of this invention provides a non absorbent, liquid impervious midspan of the shield surrounded by absorbent material such that a urinary discharge will be intercepted by the non absorbent midspan and the liquid is retained between the user's body and the midspan until the liquid is brought into contact with the surrounding absorbent, there to be absorbed and contained.

The shield of ROMANS-HESS is provided with embossed fold lines to assist the body of the user in forming the characteristic figure 8 shape (more accurately hyperbolic parabaloid) when the legs of the user are brought together.

In counterdistinction the shield of this invention is given the characteristic figure 8 shape when the two side bands of the shield are brought together by the bringing together of the legs of the user.

It can be seen by the above brief description of the prior art that when broad terminology is used to describe them, that certain functions of the instant invention can be found in the prior art, but it would be unreasonable in the extreme to allege that the prior art teaches or suggests the shield of this invention.

BRIEF DESCRIPTION OF THE INVENTION

The invention in its simplest form is a shield having an elongate, substantially rectangular shape having a broad body side surface and an opposite garment side surface. The shield has a flexible liquid impermeable non absorbent substrate that is coextensive with the shape of the shield and the substrate has absorbent strips secured to the outside perimeter of the substrate on the body side of the substrate. In use the shield is maintained in contact with the wearer's anatomy by a suitable support means.

The mode of operation of the shield is illustrated by the following example.

EXAMPLE

Two 3 inch by 4 inch (12 square inches) rectangles are cut from the same sample of substantially uniform thickness absorbent material. One of the two samples is cut into 2 strips 1 inch wide and 4 inches long and 2 strips 1 inch wide and 2 inches long. The strips are arranged to form a square that is 4 inches on a side and defining a 2 inch square reservoir surrounded by 1 inch wide strips of absorbent. The uncut rectangle and the square formed from the strips of the cut rectangle are placed a short distance (6") apart on a smooth flat and level surface.

The absorbent capacity of the material having been previously determined, two beakers are filled with a quantity of liquid equal to between 80 and 90 percent of the liquid holding capacity of the two absorbent samples. The beakers are placed in a holder which permits the pouring of both beakers at the same rate at the same time. The beakers are poured into the center of both samples as fast as the beakers can be poured without the liquid splashing.

For all materials tested in this way, the results are consistent. That is, if the liquid was poured fast enough, it will overflow the uncut sample and escape outside the perimeter of the absorbent material while the cut sample will contain the excess flow within the absorbent perimeter until it can be absorbed and thereby collected and contained within the absorbent perimeter.

A complete discussion of the physics of the demonstration of this example would make this disclosure prolix. It will suffice to observe that in the cut configuration the absorbent filled from the bottom up while in the uncut configuration the absorbent filled from the top down and that the cut sample exposed more absorbent surface to liquid earlier in the take up cycle and thereby was able to take up liquid faster than the uncut sample. It is also instructive to observe that no liquid escaped past the absorbent strips by passing between the strips and the surface upon which they were resting. This principle, demonstrated in this example, functions in use when the absorbent strips of this invention are caused to lie evenly on the skin of the wearer and thereby prevent liquid from passing between the absorbent and the skin of the user.

BRIEF DESCRIPTION OF THE DRAWINGS

FIG. 7 is a cross sectional elevational view of the isthmus section of the shield of FIG. 6.

FIG. 8 is a transverse cross section of the shield of FIGS. 5 and 6 illustrating the reservoir.

FIG. 9 is a pictorial view of the shield of this invention partially folded.

FIG. 10 is a pictorial view of the unit of FIG. 10 completely folded.

FIG. 11 illustrates the provision of grooves in the shield's absorbent components.

DETAILED DESCRIPTION OF THE INVENTION

In the figures the thickness of layers of materials and the spacing between layers of materials has been exaggerated for the purpose of clarity of illustration.

Also, in the figures like numbers refer to like objects.

Figure 1:
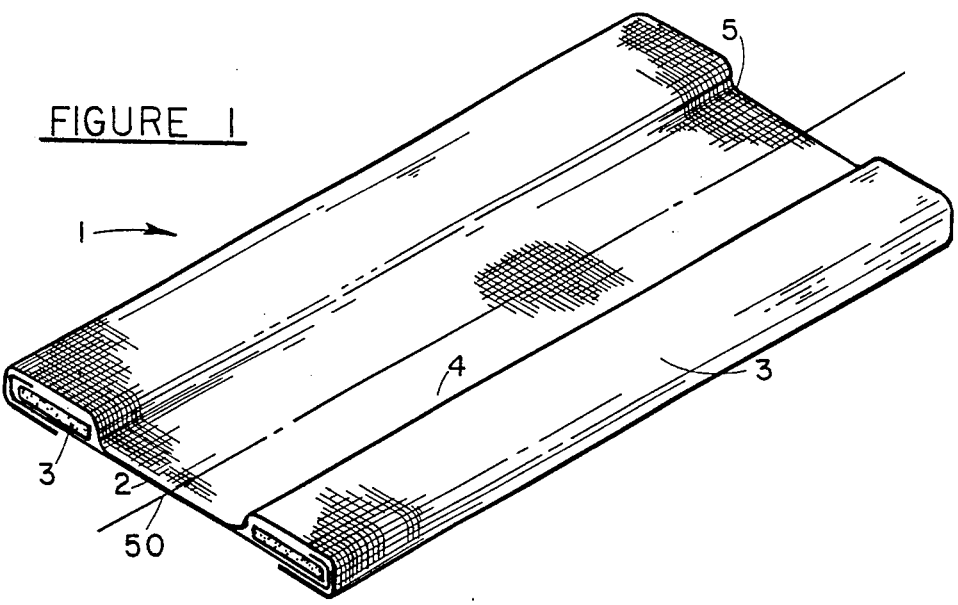
FIG. 1 is a pictorial view of the shield of this invention in one of its simplest forms.
Figure 2:
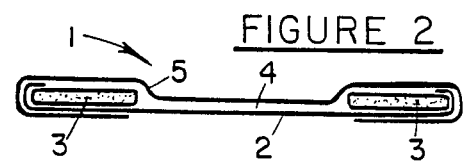
FIG. 2 is a lateral cross sectional view of the shield of FIG. 1.
Figure 3:
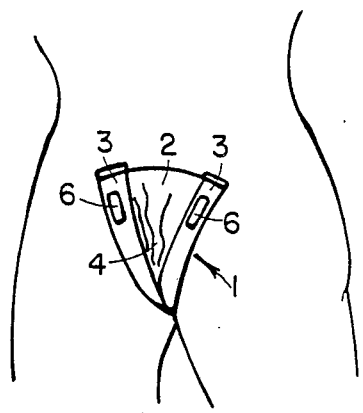
FIG. 3 is a pictorial view of the shield of FIG. 1 as it might appear in place on the anatomy of a user.

Referring now to FIGS. 1 through 3 in which the shield of this invention is shown in a simple form. Shield 1 is underlaid by baffle 2 having absorbent side bands 3 secured to its outside longitudinal edges. The broad surface of the shield having the absorbent side bands 3 secured thereto is designated the body side and the opposite broad surface is designated the garment side.

The above described shield represents a minimal assembly for practicing this invention.

In FIGS. 1 and 2, baffle 2 is shown to be folded over side bands 3 so as to cover approximately the outside one third of the body side surface of absorbent side bands 3. The provision of a "wrap around baffle" is old in the art and serves to prevent liquid from escaping the outside edge of the shield. Shield 1 is also shown to have the body side overlaid with a liquid permeable non absorbent liner 5. The provision of a "stay dry liner" is old in the art and serves to give the shield a sense of dryness.

In FIG. 3 shield 1 is shown to be provided with adhesive attachments 6 which are located at the ends of side bands 3. Adhesive attachments 6 serve to attach shield 1 to a supporting undergarment.

Figure 4:
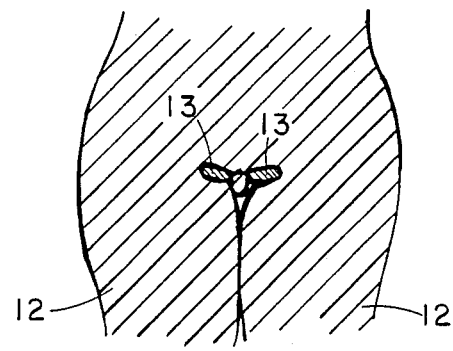
FIG. 4 is a vertical transverse section of the view of FIG. 3.
Figure 5:
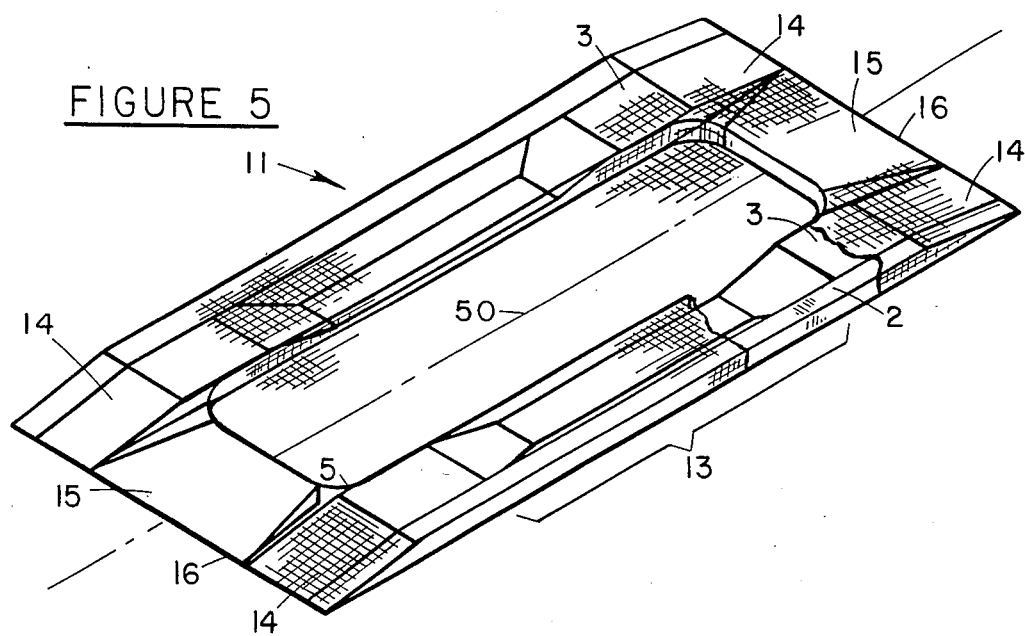
FIG. 5 is a pictorial partially broken out sectional view of a preferred embodiment of the shield of this invention.

Referring now to FIGS. 4 and 5. In order to achieve reliable performance, comfort, and discreetness the elements of shield 1 may be modified to include many embodiments and variants of novel features described below.

In FIG. 5 shield 11 is shown to be provided with a number of additions and modifications to shield 1 of FIG. 1. These additions and modifications may be provided individually or in combination.

The section of shield 11 that is to be positioned between the legs 12 of the wearer is designated isthmus section 13. Isthmus section 13 of side bands 3 can contribute significantly to the comfort and performance of shield 11.

When the legs of the average person are brought together, there is no space between the legs. Therefore any bulk placed between the legs must be accommodated to by the soft tissue of the upper thighs and the perineal body being displaced. A bunched or wadded mass between the legs can be very uncomfortable. As illustrated in FIG. 4, the preferred configuration is one wherein the side bands 3 at isthmus section 13 are of the minimal thickness that is consistent with functionality and the combined width of isthmus sections 13 is equal to or less than the width of the perineal body (2 inches to 2.5 inches). When legs 12 are brought together, the inner aspects of the upper thighs will then encompass the isthmus sections 13 as shown rather than bunch or wad the absorbent which would otherwise be expected.

In addition to decreasing the width and thickness of side bands 3 at the isthmus section 13, side bands 3 may be provided with feathered ends 14. Feathering of the ends 14 of side bands 3 provides a smooth transition from shield to body and reduces the "visibility" of the shield when it is worn under a close fitting garment.

Shield 11 may be provided with end bands 15. End bands 15, with side bands 3 form a closed perimeter of absorbent material around the body side of shield 11. The closed perimeter surrounds the flexible midspan 4 and creates a reservoir of midspan 4 in combination with the surrounding absorbent material.

End bands 15 are preferably keystoned with the longest parallel edge 16 positioned along the outside of the shield. The keystoning of end bands 15 permits side bands 3 to be bowed inward when shield 11 is placed between the legs while permitting end bands 15 and side bands 3 to lie smoothly along the body contours without bunching or wadding.

End bands 15 may be feathered towards the longest parallel edge 16 so as to provide a smooth transition between the pad contours and the body contours and thereby reduce the visibility of shield 11 when it is worn under close fitting garments.

The reduction of width and thickness of side bands 3 in isthmus section 13 and the featured ends 14 and the feathered edge 16 of end bands 15 may be achieved by the cutting away or otherwise removing of material. Alternatively, these shapes may be achieved by embossing and compressing a uniform cross sectional profile of absorbent material. Compressing the material in locations such as isthmus section 13 such that the material will swell when wet permits the provision of low dry bulk but high wet capacity in isthmus section 13. The contoured shapes described above may also be achieved by three dimensional forming techniques such as pocket forming.

Figure 6:
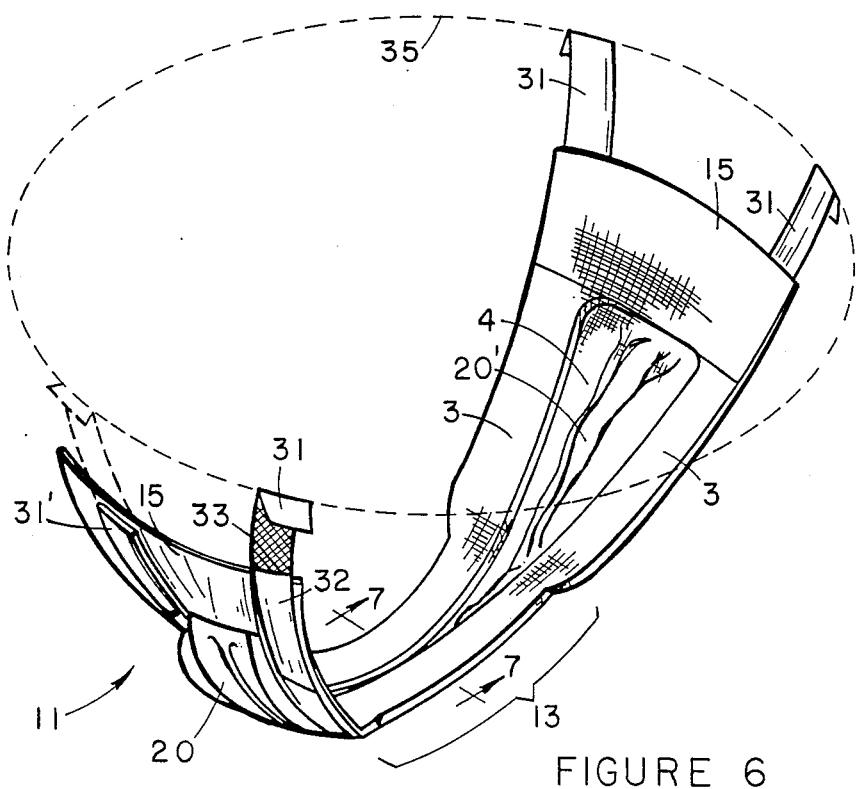
FIG. 6 is a pictorial view of the shield of FIG. 5 in the configuration it might be in when being worn.

Referring now to FIGS. 6, 7, and 8. FIG. 6 illustrates the "figure-8" shapes which shields placed between the legs are given by the anatomy of the user. The end bands 15 and side bands 3 form the absorbent perimeter of anterior reservoir 20 and posterior reservoir 20'. As side bands 3 are bowed towards each other flexible midspan 4 is bloused to form reservoirs 20 and 21'. Anterior reservoir 20 may be given sufficient capacity to accommodate comfortably to the male genitalia. Indeed, shield 11 may serve the function of an athletic supporter.

Referring now to FIG. 7. When the legs of the wearer are together, shield 11 is pressed into a closed configuration and very little anterior-posterior flow of liquid is possible. However, when the legs are parted slightly, isthmus sections 13 move slightly apart and flexible midspan 4 blouses to form longitudinal channel 21 which permits anterior-posterior flow of liquid so as to promote the longitudinal distribution of liquid and reduce the potential for lateral escape of free liquid.

Referring now to FIG. 8. Shield 11 is here shown to be positioned on the abdomen 30 of a wearer. Side bands 3 lie closely along the contours of abdomen 30, and flexible midspan 4 is bloused to form anterior reservoir 20 which is bounded by midspan 4 and abdomen 30 with absorbent side bands 3 completing the closure at each side of the reservoir. As demonstrated in the example presented above, liquid will not pass between a non absorbent surface and an absorbent band lying closely in conformance with that surface but the liquid will be absorbed into the absorbent.

Referring again to FIG. 6, extendable tabs 31 are shown to extend from the corners of shield 11 to waist band 35 of a garment shown in dashed lines. Extendable tabs 31 have a release portion 32 and an adhesive portion 33 and prior to use, adhesive portion 33 is folded upon release portion 32 as shown by folded tab 31'. Extendable tabs 31 provide two utilities not heretofore provided in the incontinent shield art. First they provide a means for adhesively attaching an incontinence shield to a support garment without the resort to peel off release strips which are a nuisance to disperse of in public facilities and second extendable tabs 31 are secured to the garment at the waist line where they can be accessed to adjust the positioning of the shield by inserting the thumbs under the waist band and using the same adjusting motions as is commonly used to adjust the waist of an ordinary garment thereby keeping the presence of an incontinence shield secret.

The shield of this invention may be supported, as a garment, by the use of a pair of elastic straps each strap joining a front corner to a back corner on the same side, and passing around the outside of the hip on that side.

Referring now to FIGS. 9 and 10 wherein a method of folding shield 11 is shown. Heretofore, incontinence shields have been of a construction that did not readily permit the shield to be folded for convenient packaging, carrying, and concealing.

Side band 3 of shield 11 are first folded onto the body side of shield 11 and shield 11 is then folded along its longitudinal center line to form a unit that is the length of the shield and has a width equal to the width of side bands 3 and a thickness approximately 4 times the thickness of shield 11. The unit is then folded across side bands 3 and perpendicular to the longitudinal folds. It has been found that both 3 and 4 folds are practical to produce a unit that is either one third or one fourth the length of shield 11 and either 12 times or 16 times the thickness of shield 11.

Referring now to FIG. 11 wherein the provision of side bands 3 and end bands 15 with transverse grooves is illustrated. It is well known in the incontinence shield art that the close fitting shields having a continuous film baffle do not readily permit air circulation with the result that a heat buildup and the attendant discomfort are often reported.

As illustrated in FIG. 11, side bands 3 and end bands 15 may be provided with transverse grooves 40 which will permit the flow of air between the body of the wearer and shield 11. Grooves 40 contribute to comfort when shield 11 is dry. When liquid reaches side bands 3 and/or end bands 15, liquid entering grooves 40 will contact the absorbent which defines grooves 40, and be absorbed thereby. Grooves 40 contribute to comfort and rate of liquid take up but do not provide an escape route for liquid as might be expected by those not skilled in the art.

Shields 1 and 11 are shown to have a center line 50 about which the shields are symmetrical. Shields 1 and 11 are also shown as substantially rectangular. It is within the scope of this invention to provide shields 1 and 11 with a keystoned shape and/or to round the corners and provide curved edges.

The invention in its simplest form, preferred embodiments, and the best mode of practicing the invention known to the inventor have been disclosed above. To disclose all the variants and combinations of the novel elements of this invention would greatly multiply the drawings and cause the specifications to become prolix. Therefore, the scope of this invention should not be limited to that which is disclosed above but should be limited only by the appended claims and all equivalents thereto which would become apparent to one skilled in the art.

I claim:

1. A protective shield to be worn between the legs comprising;
   (a) an elongate liquid impermeable flexible substrate having a longitudinal center line and having longitudinal side edges to either side of the center line and the side edges lie in the same direction as the center line and the side edges intersect lateral end edges which lie transverse to the center line and a broad surface of the substrate is designated the body side and the opposite broad surface of the substrate is designated the garment side, and
   (b) absorbent side bands secured to the body side of the substrate so as to lie along the side edges of the substrate and thereby define the absorbent side boundaries of a flexible midspan of the substrate.

2. The shield of claim 1 wherein the shield is a disposable shield and the substrate is a non absorbent substrate.

3. The shield of claim 2 wherein the shield is provided with a means for joining the shield with a shield support means wherein the joining means are positioned on the shield near the ends of the side bands and the combined shield and support means interact so that the movement of the wearer's body on one side of the longitudinal center line of the shield will not be transmittable by way of the midspan to the portion of the shield to the other side of the center line of the shield.

4. The shield of claim 3 wherein absorbent end bands are secured to the body side of the substrate so as to lie along the transverse end edges of the substrate and to span the distances between the side bands so as to, with the side bands, define a closed absorbent outside perimeter around the body side of the shield and the perimeter has within its boundaries a midspan of flexible substrate.

5. The shield of claim 4 wherein the side bands and the end bands are separate absorbent segments and the end bands are keystone shaped having the longer of the non converging edges of the end band attached to the body side of the substrate along the end edges of the shield.

6. The shield of claim 3 wherein the substrate is folded over the outside edges of the side bands so as to overlay at most, one third of the body side surfaces of the side bands.

7. The shield of claim 3 wherein the body side of the shield and a portion of the garment side of the shield are overlaid with a liquid permeable, non wettable liner.

8. The shield of claim 4 wherein the end bands are feathered so that the absorbent is relatively thin in the area adjacent to the end edges of the shield and relatively thick in the areas adjacent to the flexible midspan.

9. The shield of claim 4 wherein the ends of the side bands are feathered so that the absorbent is relatively thin adjacent to the end edges of the shield and is relatively thick at locations adjacent to the flexible midspan.

10. The shield of claim 3 wherein the side bands are reduced in width in those portions of the side bands that will, in use, be positioned relative to the user's anatomy in the isthmus between the intersection of the perineal body with the inguinal fold and the intersection of the perineal body and the gluteal fold.

11. The shield of claim 3 wherein the side bands are reduced in thickness in those portions of the side bands that will, in use, be positioned relative to a user's anatomy between the intersection of the perineal body with the inguinal fold and the intersection of the perineal body and the gluteal fold.

12. The shield of claim 4 wherein the absorbent elements of the shield are given contoured shapes by means of cutting and embossing techniques.

13. The shield of claim 4 wherein the absorbent elements of the shield are given contoured shapes by three dimensional forming techniques.

14. The shield of claim 3 wherein the support means are strips of contact adhesive positioned near the ends of the side bands on the garment side of the shield and whereby the shield may be adhesively attached to a garment.

15. The shield of claim 3 wherein the support means are adhesive tabs secured to the shield near the ends of the side bands and the tabs are extendable beyond the perimeter of the shield in the direction of the longitudinal axis of the side bands and the tabs are provided with contact adhesive by means of which the tabs may be secured to a garment at a location near the waist band of the garment.

16. The shield of claim 3 wherein the support means are elasticized bands which are joinable to the shield near each end of each side band so as to form bands that traverse the hips of the wearer and join the ends of the side bands on each side of the longitudinal center line of the shield so as to form a self supporting garment.

17. A protective shield to be worn between the legs comprising;

(a) an elongate substantially rectangular shape having a longitudinal axis wherein the shape is symmetrical about the longitudinal axis, and (b) the shape having two broad surfaces; a body side surface and garment side surface, and (c) a flexible substrate underlying the shield on the garment side of the shield, and (d) absorbent side bands secured to the body side of the shield, and the side bands lying parallel to the longitudinal center line and along the longitudinal side edges of the rectangular shape, and (e) the side bands have a width approximately one fourth of the lateral dimension of the rectangular shape.

18. A method of folding the shield of claim 17 comprising the steps of;

(a) folding the side bands onto the body side of the shield to form a sub assembly one half the width of the unfolded shield, (b) folding the sub assembly along the longitudinal center line of the shield to form a unit that is approximately the length of the shield long, the width of the side bands wide and four times the thickness of the shield, (c) folding the unit into three equal longitudinal segments with the folds being across the side bands and perpendicular to the longitudinal folds so as to form a unit that is approximately one third as long as the unfolded shield, the width of the side bands and twelve times the thickness of the shield, and (d) the folded unit being discreet and readily carried in a pocket or purse.

19. A method of folding the shield of claim 17 comprising the steps of;

(a) folding the side bands onto the body side of the shield to form a sub assembly one half the width of the unfolded shield, (b) folding the sub assembly along the longitudinal center line of the shield to form a unit that is approximately the length of the shield long, the width of the side bands wide and four times the thickness of the shield, (c) folding the unit into four equal longitudinal segments with the folds being across the side bands and perpendicular to the longitudinal folds so as to form a unit that is approximately one fourth as long as the unfolded shield, the width of the side bands and sixteen times the thickness of the shield, and (d) the folded unit being discreet and readily carried in a pocket or purse.

20. A protective shield to be worn between the legs comprising;

(a) an elongate substantially planar shape having a longitudinal center line and the shape is symmetrical about the center line, and (b) a first broad surface is designated the body side, and (c) a second broad surface which is designated the garment side, and (d) the shield is underlayed on the garment side by a non absorbent liquid impermeable baffle, and (e) the perimeter of the shield on the body side has secured thereto bands of absorbent material distributed so as to form a substantially closed perimeter of absorbent material which surrounds a flexible center span of non absorbent liquid impermeable substrate which, in use, serves to receive and rapidly distribute urine from the location of reception on the substrate to the surrounding absorbent material.

21. The shield of claim 20 in combination with the skin of a user wherein the bands of absorbent material are positioned so as to lie closely against the skin of the wearer so that free liquid residing between the non absorbent midspan of the shield and the skin of a wearer cannot pass over and cannot pass under the bands of absorbent material and must pass through the bands of absorbent material before reaching the outside perimeter of the shield.

22. The shield of claim 20 wherein the body side of the absorbent material has transverse depressions formed therein and the depressions communicate between the outside perimeter of the shield and the flexible midspan of the shield and the depressions, when the shield is positioned so as to lie closely against the skin of a user so as to permit air to pass between the absorbent bands of the shield and the skin of the user but to not permit liquid to pass between the bands of absorbent and the skin of a user.

* * * * *

UNITED STATES PATENT AND TRADEMARK OFFICE
CERTIFICATE OF CORRECTION

PATENT NO. : 4,753,645
DATED : June 28, 1988
INVENTOR(S) : Russell L. Johnson

It is certified that error appears in the above-identified patent and that said Letters Patent is hereby corrected as shown below:

In column 5, line 61, "featured" should read --feathered--;

In column 6, line 11, "21'" should read --20'--.

Signed and Sealed this

Seventh Day of March, 1989

*Attest:*

DONALD J. QUIGG

*Attesting Officer*   *Commissioner of Patents and Trademarks*